(12) United States Patent
Komarek et al.

(10) Patent No.: US 6,184,039 B1
(45) Date of Patent: Feb. 6, 2001

(54) METHOD FOR DETERMINING THE FAT CONTENT OF FEED, FOOD, AND OTHER MATERIALS UTILIZING FILTER MEDIA ENCAPSULATION

(76) Inventors: Andrew R. Komarek, 2033 Turk Hill Rd.; Ronald J. Komarek, 35 Teal Dr., both of Fairport, NY (US) 14450

( * ) Notice: Under 35 U.S.C. 154(b), the term of this patent shall be extended for 0 days.

(21) Appl. No.: 09/304,776

(22) Filed: May 4, 1999

(51) Int. Cl.[7] .................................................. G01N 1/00
(52) U.S. Cl. .............................. 436/23; 436/178; 73/866
(58) Field of Search ........................... 436/23, 177, 178; 73/53.01, 53.02, 866; 210/633, 634, 808; 554/8, 12–14, 16; 422/101, 277

(56) References Cited

U.S. PATENT DOCUMENTS

| | | |
|---|---|---|
| 4,184,961 | 1/1980 | Rynde et al. . |
| 4,265,860 | 5/1981 | Jennings et al. . |
| 5,017,500 * | 5/1991 | Langer ................................. 436/178 |
| 5,370,007 * | 12/1994 | Komarek ................................. 73/866 |
| 5,660,727 | 8/1997 | Gleave et al. . |

* cited by examiner

Primary Examiner—Matthew O. Savage
(74) Attorney, Agent, or Firm—Wall Marjama & Bilinski

(57) ABSTRACT

A method for simultaneous analysis of individual samples for crude fat content. This method utilizes a process of encapsulation of a sample in filter media and the batch processing of numerous samples in one vessel. The method involves the quantitative encapsulation of a sample in a filter media. Multiple samples are subsequently extracted in batch with a suitable solvent, under controlled temperature and pressure conditions. The quantitative determination of crude fat is accomplished by measuring the difference between the residue remaining in the filter media and the weight of the original sample. This method greatly improves the efficiency of crude fat determinations and allows the processing of numerous samples simultaneously saving analytical time.

17 Claims, 1 Drawing Sheet

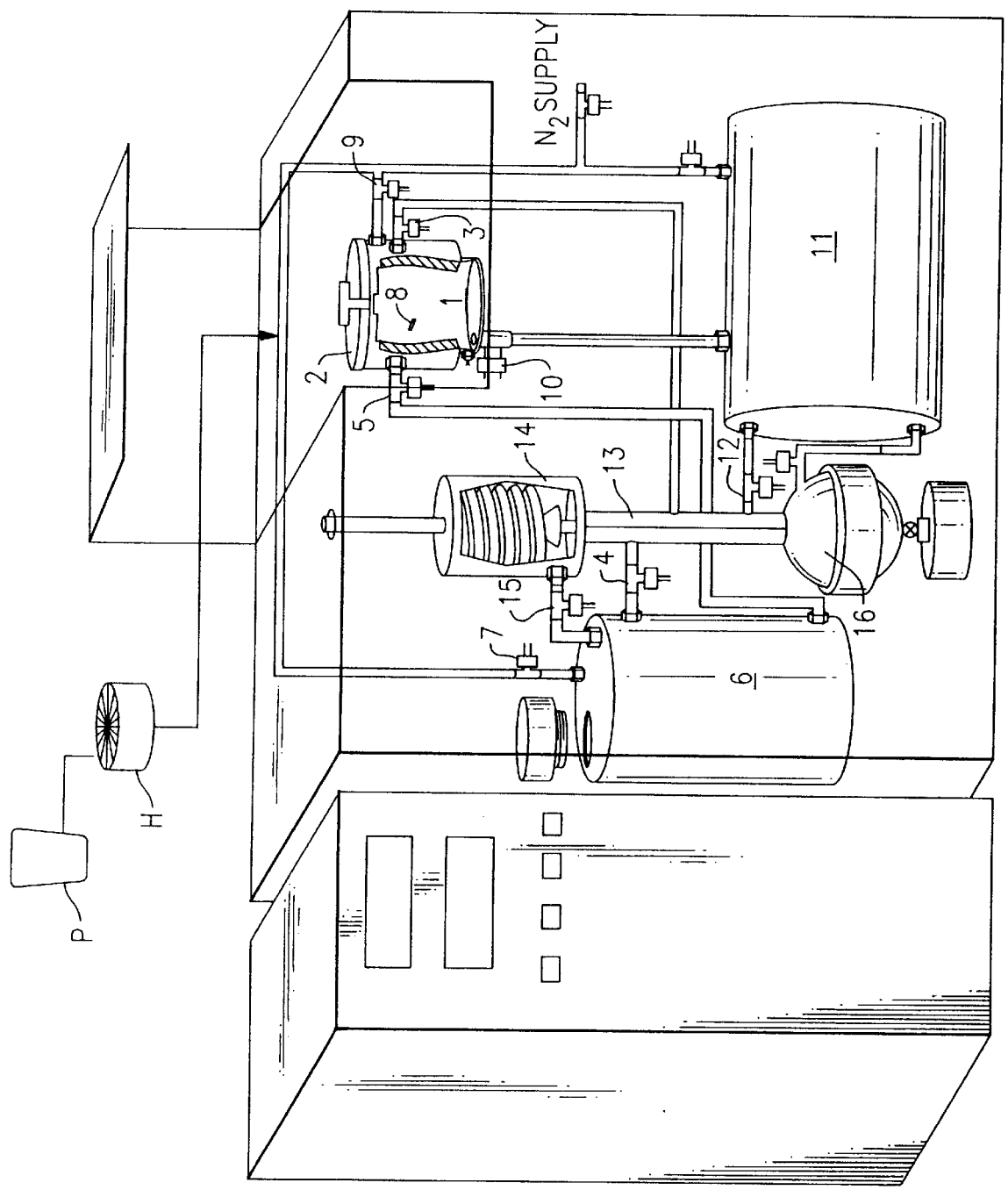

METHOD FOR DETERMINING THE FAT CONTENT OF FEED, FOOD, AND OTHER MATERIALS UTILIZING FILTER MEDIA ENCAPSULATION

BACKGROUND OF THE INVENTION

The evaluation of the nutrient composition of feeds and foods has traditionally included an analysis of crude fat. Crude fat is primarily a measure of the triglyceride content of the food or feed and represents the more energy dense component. Fat is commonly extracted from feed and food with diethyl either or petroleum ether. Compounds other than fat are soluble in diethyl ether or petroleum ether but they represent minor components in relation to the energy contribution to the diet and generally fall in the category of lipids. The quantitative analysis of crude fat has traditionally been accomplished by the Soxhlet extraction technique (Quantitative Chemical Analysis, by Hamilton and Simpson). The current state of the art of fat analysis is described in, "Methods of Analysis for Nutritional Labeling". The standardized Soxhlet technique is detailed by the Association of Official Analytical Chemists in the AOAC Official Method 920.39. This Soxhlet technique involves placing an individual sample in a filter chamber. This filter chamber is then placed in the siphoning compartment. The heater boils the solvent, commonly petroleum ether, and passes the vapor into a condenser. The condenser condenses the vapor into a liquid, channels it into the filter chamber and siphoning compartment. The solvent is periodically siphoned back into the distilling flask after it reaches a certain level in the siphoning compartment. The distillation/extraction process is continued for four to sixteen hours. The fat content of the sample is then determined either by evaporating the solvent and measuring the remaining fat directly or indirectly by weighting the weight loss of the sample contained in the filter chamber. The filter chambers that are commonly used are thimble shaped filter paper. Glass filter chambers with fritted glass filters and fritted Alundum thimbles are also used.

As described above, the prior art for crude fat analysis that is currently being used by regulatory laboratories, industry and academia involves individual analysis based on the traditional Soxhlet technique.

Apparatus designed to expedite the Soxhlet extraction process and improve the manual efficiency of the extraction process are described in U.S. Pat. No. 4,184,961. Improvements in the rate of extraction and solvent penetration of the sample matrix have been achieved by increasing the temperature and pressure of the extracting solvent as taught by U.S. Pat. No. 4,265,860. These instruments have the same limitation as the standard Soxhlet process of dealing with individual samples individually throughout the analysis. These instruments deal with individual samples in multiple setups and semi-automate or automate individual steps such as extraction, rinsing and solvent evaporation. These instruments can only process a limited number of samples since they deal with samples individually (up to twelve), and require costly equipment when calculated on a per sample basis.

In all of the systems described above, the samples are processed individually in order to yield a unique value for each sample. This requirement of individual sample processing limits the efficiency of the analysis and increases the cost of the instrument by requiring a replicate of the apparatus for each sample capable of being analyzed by the instrument.

U.S. Pat. No. 5,370,007 is directed to a Fiber Analysis System in which a sample of a feedstuff or food of a predetermined weight is sealed in a filter bag with selected porosity which recovers the fiber components while allowing the removal of the detergent soluble components of the sample. The fiber analysis taught by the '007 patent is accomplished by exposing the sample to an aqueous detergent solution (polar solvent) under heated conditions for a time sufficient to remove substantially all soluble solids from the feed while retaining the fiber components within the filter bag. The preparation of samples for analysis requires that the samples be ground to a fine particle size in order to ensure a representative aliquot. The sample grinding process fractures and fragments the different components of the feed differently. Non-fiber components such as non-structural carbohydrates, sugars, proteins, and minerals fracture into much finer particles than the fiber components. Because the large majority of fine particles are not fiber, their passage through the fiber filter media causes no error. Therefore the filtration media used in these filter bags benefits from the surface tension of the aqueous solution, and from the fact that very fine particles are soluble and do not need to be retained. To ensure accurate fiber results, only retention of particles larger than 25 microns is required for the filter media.

The significant differences between fiber analysis of the prior art and fat analysis of the present invention include: retention vs extraction of the analyte; the use of aqueous solutions vs. organic solvents; and the retention of coarse particle vs fine particle; 25 micron vs <4 micron filter media. These differences will become more apparent with a reading of the detailed description of the invention.

SUMMARY OF THE INVENTION

It is therefore an object of the present invention to provide a method of determining crude fat content of a feedstuff or food which overcomes the problems of the prior art described above.

It is another objective of the present invention to provide an efficient system for simultaneously determining the fat content of individual samples.

It is another object of the present invention to provide a system for determining the fat content of a food or feed by a novel batch processing system.

It is a further object of the present invention to improve the efficiency of performing a fat extraction.

It is also an objective of this invention to reduce the cost of the analysis and increase the capacity of a fat extraction instrument.

It is yet another objective to provide a system for processing samples in a batch which enables one instrument to perform numerous extractions simultaneously.

It is another object of the present invention to provide an effective filtering chamber that will retain very fine particles, and still provide adequate access to the exchange of solvent.

The present invention is based on the discovery that crude fat content of individual samples can be determined, in batch, by encapsulating a quantitative aliquot of each sample in the filter media and simultaneously extracting the crude fat with a suitable solvent under controlled conditions of temperature and pressure. Suitable solvents for crude fat analysis include either diethyl ether or petroleum ether. The crude fat content can then be determined by the loss in weight of the samples after rinsing and drying the sample. Other solvents, used in the determination of fat and lipids, such as methylene chloride, and mixtures of chloroform/ methanol and diethyl ether/ethanol can also be used in this invention. The filter media for other prior art techniques was not capable of performing this analysis. The success of this system of analysis using the batch process required the development of unique filter media with the capability of retaining 4 micron size and larger particles while permitting sufficient flow of the solvent to efficiently extract all the crude fat. The main advantage of the present invention over the conventional prior art is that it greatly improves the efficiency of the analysis. A technician can analyze twenty samples simultaneously, processing 200 or more samples a day.

BRIEF DESCRIPTION OF THE DRAWING

FIG. 1 is a side sectional view illustrating the apparatus for carrying out the present invention.

DETAILED DESCRIPTION OF THE INVENTION

The analyte, fat, is quantitatively extracted from the filter chamber while all other components are retained in the filter chamber. In the present invention, the fat is determined by sample weight loss after extraction of the fat. The organic solvents used in fat extraction have low surface tension allowing passage of fine particles through typical filter media. These fine particles need to be retained in the filter chamber while extracting the fat. This requirement for fat analysis was a major barrier in the development of the present invention. It required a significant advance in filter technology to retain the fine particles, while not impeding the passage of the extracting solvent. To ensure accurate crude fat results, the retention of particles as small as 4 microns is required for the filter media.

In the present invention each sample's unique identity is preserved by encapsulating it in individual compartments (filter pouches) composed of specially designed filter media. The sample is available for extraction by virtue of the permeability of the filter media. The filter media presents a barrier to the escape of the sample particulates but not to the efficient passage of the solvent carrying the dissolved fat. This encapsulation permits the analysis of numerous samples in the same vessel under controlled conditions. Conditions in the vessel can be controlled (temperature, pressure and fluid movement) so that both conventional and nonconventional (supercritical) solvents can be used. In this invention fluid movement through the filter media is enhanced by rotating the filter pouch holder during the extraction and rinsing phase of the analysis. Under certain conditions fluid movement is further enhanced by momentarily reducing the pressure in the vessel and allowing the solvent to vaporize and force the liquid out of the pouch, and then on the return to a higher pressure the pouch collapses and permits the solvent to re-enter. Solvent movement can also be enhanced by ultrasonics.

In the present invention the filter media can be produced using any technology that can produce a membrane with the characteristics of fine particle retention (at least 4 micron) and allow rapid solvent passage. These two characteristics are in opposition to their benefits for this analysis (i.e. the greater the particle retention the higher the resistance to solvent passage). The filter media must have other characteristics to properly perform its function in this analysis. These include the resistance to chemical breakdown under the conditions of the analysis. The ability to retain its spatial dimensions under the conditions of the analysis (temperature and pressure) and its ability to be completely sealed in some practical fashion (i.e. heat sealable). Suitable materials for filter media may comprise polymers such as nylon, polyethylene, polypropylene, polyesters such as polyethylene terephthalate, paper, glass, ceramics and porous metal structures. In one embodiment melt blown nylon (AET Specialty Nets, Middletown, Del.) was prepared with a density of 100 gsm and calendered to 6 mil to produce filter media capable of retaining 4 micron particles.

In the present invention crude fat analysis is performed by first tarring the filter media, which in a preferred embodiment is a pouch (approximately 2×2.25 in.), weighing a predried aliquot of the sample (1 to 3 g) into the pouch, and heat sealing the pouch closed to encapsulate the sample. Alternatively a sample can be analyzed without predrying if an accurate dry matter value is determined for the sample. Up to twenty samples are then placed in a holder where each encapsulated sample is positioned in a radial array. The holder is placed in the extraction vessel and the vessel is the sealed closed. Solvent is added to the vessel and temperature is controlled within the range of ambient to 120° C. at pressures between 0 to 100 psi. Sufficient pressure is maintained in the vessel to prevent boiling when the temperature exceeds the boiling point of the solvent. After a sufficient time for extraction has elapsed (commonly in the range of 5–30 minutes at the extraction temperature), the solvent is evacuated from the vessel and the samples are rinsed with pure solvent several (2–3) times. Used solvent can be re-distilled for further use. After the samples have been removed from the extraction chamber and traces of the solvent have been completely removed from the sample by evaporation, the samples are dried in an oven at 100° C. and weighed. The loss of weight due to the extraction is the measure of crude fat. This system for fat analysis is a suitable substitute for the standard Soxhlet or accelerated Soxhlet methods. The method can be used for all samples commonly analyzed by the Soxhlet method. These include animal feeds, pet foods, human foods and other materials that contain fats and oils. Animal feeds include plant material such as roughages, cereal grains, high fat and high protein feeds such as soybeans, cottonseeds and byproduct feeds such as high protein oil meals and mill byproducts. Pet foods for dogs and cats include individual ingredients such as meat scraps, processed meats and cereal grains and other plant products. Human foods include individual food ingredients i.e., foodstuffs, of plant and animal origin such as cereal grains, process cereals and foods, processed meats and meat products.

The simultaneous analysis of multiple samples greatly increases the number of fat determinations that a technician can process in a given period of time. The present invention eliminates the required prior art solvent evaporation step, the fat transfer step, and the drying and weighing of the fat residue. The sealed extraction vessel virtually eliminates laboratory emissions of the solvent and increases the safety of handling volatile, flammable solvents.

The following example illustrates a preferred system for carrying out the present invention.

EXAMPLE

Filter media made from melt blown nylon is fashioned in the form of a pouch P approximately 2×2.25 in. as illustrated in FIG. 1. The pouch is made of a melt blown nylon having a density of 100 gsm and calendared to 6 mil to produce a filter media capable of retaining 4 micron particles and is available from AET Specialty Nets of Middletown, Del. A 1.0 g±0.1 g sample of feedstuff (not shown) is weighed into the tared pouch and sealed closed in the filter media, encapsulating the sample. The encapsulated sample is placed in a pouch holder H that aligns the pouches in a vertical position. The holder positions twenty encapsulated samples in a radial array. Up to twenty samples can be processed simultaneously in the extraction vessel 1. After the extraction vessel lid 2 is sealed, the instrument fills the vessel 1 with petroleum ether (boiling point range 35° to 65° C.). Filling occurs when the extraction vessel vent valve 3 is opened, the solvent reservoir vent valve is closed, the solvent transfer line valve 5 is opened and the solvent reservoir 6 is pressurized with nitrogen. Opening the solvent reservoir nitrogen valve 7 pressurizes the solvent reservoir 6. The solvent line transfer valve 5 is closed when the level sensor 8 indicates the chamber is filled to the proper level. The extraction vessel nitrogen valve 9 is opened to purge head space of the vessel 1. The nitrogen valve 9 is then closed and the valve 3 is closed to seal the vessel. The temperature of the vessel 1 is thermostatically controlled at 90°±1.0 C. and the pouch holder is rotated at a rate of 25 rpm. Samples of dog food, swine feed, catfish food and chicken meat meal were analyzed in triplicate in a single batch. The analysis was replicated in a second batch and the results of the six analyses for each of the four samples is presented in the following table. The first three samples were from the Association of American Feed Control Officials (aafco) check sample program. After extraction is complete 10 minutes at temperature the drain valve 10 is opened exhausting the solvent into the waste chamber 11 while the waste chamber vent valve 12 is open. A portion of the solvent vaporizes and passes out of the waste chamber vent valve 12 into the reflux column 13. The vapors pass into the condenser 14 and are returned to the solvent reservoir 6 by opening the condenser valve 15. The samples are rinsed two times by filling the vessel with solvent in the same manner as before. The samples are removed from vessel 1 and the residual solvent is allowed to evaporate from the pouches in a fume hood. The samples are dried in an oven at 104° C. for 3 hours and weighed. The quantity of fat is determined by the loss of weight that the sample has incurred during the extraction corrected for the moisture content of the sample. During the function of the instrument, the distillation chamber 16 is heated and the waste solvent is vaporized, condensed and collected in the solvent reservoir 6.

A series of feed/food samples were analyzed for crude fat using the system described in the above Example. The results were compared with crude fat values determined by the standard Soxhlet procedure utilizing petroleum ether. The crude fat results are summarized in the following table.

| | | DATA TABLE | | | | | |
|---|---|---|---|---|---|---|---|
| | | CRUDE FAT | | | | | |
| | | STANDARD SOXHLET | | | BATCH ENCAPSULATION | | |
| FEED TYPE | ID # | % FAT | SD | CV | % FAT | SD | CV |
| Dogfood | 9822 | 5.54 | 0.134 | 2.42 | 5.50 | 0.120 | 2.19 |
| Swine feed | 9823 | 4.87 | 0.135 | 2.77 | 4.81 | 0.150 | 3.13 |
| Catfish food | 9821 | 4.62 | 0.178 | 3.85 | 4.74 | 0.381 | 8.04 |
| Chicken meal | #6 | 42.91 | | | 42.44 | 0.529 | 1.25 |

The results indicate that the present invention produces analytical data comparable to a well run soxhlet analysis but with far greater efficiency. Furthermore, there are no statistically significant differences between the standard Soxhlet technique and the batch encapsulated technique.

The foregoing examples and methods have been described in the specification for the purpose of illustration and not limitation. It should be understood that other modifications and ramifications of the present invention will occur to those skilled in the art based upon this disclosure and are intended to be within the scope of this invention.

What is claimed is:

1. A method for determining the crude fat content of a foodstuff sample which comprises:

providing a quantitative aliquot (sample) of said foodstuff sample encapsulated in a filtering material to define a filtering chamber with a predetermined capability of retaining the sample particles and sufficient porosity for organic solvent penetration;

exposing the encapsulated sample to organic solvent in an extraction vessel for sufficient time to extract substantially all of said fat contained in the encapsulated sample, with the balance of the sample components remaining encapsulated;

rinsing the encapsulated sample with the solvent to remove any residual fat in the encapsulated sample; and weighing the encapsulated sample and determining the fat content of the sample by the loss of weight of the sample.

2. The method of claim 1 in which the filter chamber is in the form of a sealed pouch having a filtering capacity capable of retaining 4 micron particles.

3. The method of claim 1 in which the filter material used for encapsulation, shaped in the form of a pouch is made of at least one material selected from the group consisting of, polymers, nylon, polyethylene, polypropylene, polyesters, polyethylene terephthalate, and paper.

4. The method of claim 1 in which the process is carried out at a pressure of about 0 to 100 psi at a temperature in the range of ambient to 120° C.

5. The method in claim 1 in which the foodstuff includes roughages, cereal grains, soybeans, and cottonseeds.

6. The method of claim 1 in which the foodstuff includes meat and cereal grains.

7. The method of claim 6 in which the process is carried out at a pressure of about 0 to 100 psi at a temperature in the range of about ambient to 120° C.

8. The method of claim 1 in which the filtering chamber is made of at least one material selected from the group consisting of fiberglass, polyethylene, polypropylene, polyethylene terephthalate, polyesters, paper, glass, ceramics, and porous metal structures.

9. The method of claim 1 in which a plurality of samples are simultaneously treated in batch.

10. A method of determining the crude fat content of a foodstuff sample which comprises:

providing a quantitative aliquot of said foodstuff contained within an enclosed filtering media having a predetermined capability of retaining particles of said sample and sufficient porosity for organic solvent penetration, and where said filtering media is in the form of a sealed pouch having a filtering capacity capable of retaining 4 micron size particles;

placing said pouch within a sealed extraction vessel;

exposing said pouch to organic solvent for sufficient time to extract substantially all of said fat contained in the sample from said chamber, with the balance of the sample components remaining in said pouch;

rinsing the pouch and contents with the solvent to remove any residual fat in the sample and pouch; and weighing the pouch with the sample and determining the fat content of the sample by the loss of weight of the sample.

11. The method of claim 10 in which the pouch is made of at least one material selected from the group consisting of fiberglass, polyethylene, polypropylene, polyethylene terephthalate and, polyesters.

12. The method of claim 10 in which the process is carried out at a pressure of about 0 to 100 psi at a temperature in the range of about ambient to 120° C.

13. The method of claim 10 in which a plurality of samples are simultaneously treated in batch.

14. A method of determining the crude fat content of a plurality of a foodstuff sample which comprises:

providing a quantitative aliquot of said foodstuff each individually encapsulated within a sealed filtering media having a predetermined capability of retaining the sample particles and sufficient porosity for organic solvent penetration;

placing said filtering media within a sealed extraction vessel;

exposing the filtering media to a heated organic solvent, for sufficient time to extract substantially all of said fat contained in the samples from said media, with the balance of the sample components remaining in said sealed media;

rinsing the filtering media and contents with the solvent to remove any residual fat in the samples and filtering media; and weighing the filtering media with the sample and determining the fat content of the samples by the loss of weight of the sample.

15. The method of claim 14 in which the filter media is in the form of a sealed pouch having a filtering capacity capable of retaining 4 micron particles.

16. The method of claim 15 in which the pouch is made of at least one material selected from the group consisting of fiberglass, polyethylene, polypropylene, polyethylene terephthalate and, polyesters.

17. The method of claim 14 in which the process is carried out at a pressure of about 0 to 100 psi at a temperature in the range of about ambient to 120° C.

* * * * *